United States Patent
Rinck et al.

(10) Patent No.: US 7,920,734 B2
(45) Date of Patent: Apr. 5, 2011

(54) METHOD FOR VISUALIZATION OF PLAQUE DEPOSITS FROM 3D IMAGE DATA RECORDS OF VESSEL STRUCTURES

(75) Inventors: Daniel Rinck, Forchheim (DE); Michael Scheuering, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1609 days.

(21) Appl. No.: 11/220,667

(22) Filed: Sep. 8, 2005

(65) Prior Publication Data
US 2006/0171585 A1 Aug. 3, 2006

(30) Foreign Application Priority Data
Sep. 9, 2004 (DE) .................... 10 2004 043 676

(51) Int. Cl.
G06K 9/32 (2006.01)
G06K 9/48 (2006.01)
(52) U.S. Cl. .................... 382/131; 382/300; 382/199
(58) Field of Classification Search .................. 600/300, 600/407; 382/100, 128, 129, 130, 131, 132, 382/133, 134, 173, 181; 128/920; 378/1, 378/37, 21, 41, 42, 38, 44, 51, 62, 65, 146
See application file for complete search history.

(56) References Cited

U.S. PATENT DOCUMENTS

| | | | |
|---|---|---|---|
| 4,945,478 A | | 7/1990 | Merickel et al. |
| 6,463,167 B1 * | | 10/2002 | Feldman et al. ............. 382/128 |
| 6,466,687 B1 * | | 10/2002 | Uppaluri et al. ............. 382/128 |
| 2002/0136440 A1 * | | 9/2002 | Yim et al. .................... 382/131 |
| 2004/0022359 A1 * | | 2/2004 | Acharya et al. ............ 378/98.11 |
| 2004/0066958 A1 * | | 4/2004 | Chen et al. ................... 382/128 |
| 2004/0249270 A1 * | | 12/2004 | Kondo et al. ................. 600/425 |
| 2005/0043614 A1 * | | 2/2005 | Huizenga et al. ............ 600/427 |
| 2005/0080328 A1 * | | 4/2005 | Vass et al. .................... 600/407 |
| 2006/0241427 A1 * | | 10/2006 | Kinouchi et al. ............ 600/437 |
| 2007/0019846 A1 * | | 1/2007 | Bullitt et al. ................. 382/128 |
| 2007/0019850 A1 * | | 1/2007 | Knoplioch et al. .......... 382/131 |

OTHER PUBLICATIONS

Hull, J.W, Definition of Stenosis in Parent's Common Sense Encyclopedia, Publication date May 13, 1998, Available Online at Internet archive: http://web.archive.org/web/19980513100554/http://drhull.com/EncyMaster/index.html.*
German Office Action dated Jun. 16, 2005.

* cited by examiner

Primary Examiner — Bhavesh M Mehta
Assistant Examiner — Tahmina Ansari
(74) Attorney, Agent, or Firm — Harness, Dickey & Pierce, P.L.C.

(57) ABSTRACT

A method is disclosed for visualization of plaque deposits from 3D image data records of vessel structures, in particular of the coronary vascular system, in which at least one predeterminable section of the vessel structure with the plaque deposits is segmented in the 3D image data record in order to obtain segmented 3D image data. A synthetic 3D model image of the at least one section of the vessel structure and of the plaque deposits is produced from the segmented image data, and includes only boundary surfaces of the vessel structure and of the plaque deposits. The synthetic 3D model image is produced by three-dimensional interpolation between pixels which are associated with boundary surfaces of the vessel structure, and between pixels which are associated with boundary surfaces of the plaque deposits in order to obtain a uniform grid at pixels for the 3D model image. Finally, the synthetic 3D model image or a partial volume of it is visualized. The method allows a vessel section with plaque deposits to be visualized better for evaluation.

20 Claims, 2 Drawing Sheets

METHOD FOR VISUALIZATION OF PLAQUE DEPOSITS FROM 3D IMAGE DATA RECORDS OF VESSEL STRUCTURES

The present application hereby claims priority under 35 U.S.C. §119 on German patent application number DE 10 2004 043 676.2 filed Sep. 9, 2004, the entire contents of which is hereby incorporated herein by reference.

FIELD

The present invention generally relates to a method for visualization of plaque deposits from 3D image data records of vessel structures, in particular of the coronary vascular system, in which at least one section of the vessel structure with the plaque deposits is segmented in the 3D image data record in order to obtain segmented image data.

BACKGROUND

Vessel structures can be visualized very well in particular using computed tomography (CT) techniques after injection of a contrast agent. Modern multiple-layer CT systems allow the recording and display of vessel structures with relatively high three-dimensional resolution, as is very important in particular for visualization of coronary vessel structures.

On the basis of the recorded 3D image data record, the user, when presented with a suitable visualization, can determine the relationship between the vessel lumen and the plaque deposit on the vessel, in order from this to estimate the risk of the patient having an infarct. The subsequent steps for treatment of the patient are then defined as a function of the result of this evaluation.

In this case, the 3D image data record of the examination volume in which the vessel structure is located is generally evaluated by means of standard visualization techniques, such as MPR (multiplanar reformatting) or using axial slice images along the central axis of the vessels. In these methods, the viewer is presented with the recorded 3D image data in the desired projection or in the desired slice plane, possibly after segmentation of the vessel structure, on a monitor. The three-dimensional relationship between the plaque deposit and the vessel lumen and thus the degree of stenosis are in this case generally determined on the basis of a display in the form of an image of the entire examination volume.

U.S. Pat. No. 4,945,478 A describes an image processing system for identification and 3D display of atherosclerotic deposits from MRT data records. For this purpose, the vessels are extracted by way of segmentation from the image data record, and plaque deposits are identified in the image data. The plaque deposits are classified in the method from this document in order to make it possible to visualize the different classification in the subsequent display.

The 3D visualization is produced on the basis of a "quadtree" display, in which the entire volume of interest is subdivided into cuboids, with each cuboid being allocated a specific brightness or color, which represents the corresponding classification of the plaque. In this case one or more of the original pixels in each cuboid is or are combined so as to also reduce the number of data items to be processed overall.

SUMMARY

An object of at least one embodiment of the present invention is to specify a method for visualization of plaque deposits from 3D image data records of vessel structures, which method allows improved evaluation.

An object may be achieved by a method. Advantageous refinements of the method can be found in the following description as well as the example embodiment.

In the case of at least one embodiment of the method for visualization of plaque deposits from 3D image data records of vessel structures, in particular of the coronary vascular system, at least one section of the vessel structure with the plaque deposits is first of all segmented in the 3D image data record in order to obtain segmented 3D image data. The segmented 3D image data is now not displayed using a projection or slice plane which can be predetermined, in contrast to the known visualization techniques. In fact, the segmented image data is first of all used to produce a synthetic 3D model image of the selected section of the vessel structure and of the plaque deposit.

This model image includes only the respective boundary surfaces of the vessel structure, that is to say the vessel walls, and the plaque deposits. The synthetic 3D model image or a partial volume of it which can be selected is then visualized for the user.

The user now has the capability to analyze the displayed model image interactively, for example by selection of the perspective or slice plane to be displayed or by rotation, shifting or enlargement of the display. Furthermore, it is possible for the viewer to move virtually through the display (fly through) in order in this way to record the relationships within the individual vessels. Since the 3D model receives only the corresponding boundary surfaces of the vessels and of the plaque deposits, the plaque component relative to the vessel lumen can be determined directly at any time, in a simple manner.

The provision of an artificially produced 3D model of the relevant boundary surfaces furthermore allows very rapid image processing with an interactive movement within the display. If required, at least one embodiment of the method also allows the production and visualization of a 3D model image of the entire vessel structure contained in the 3D image data record, if this is necessary.

The vessel structure and the plaque deposits can be segmented using known segmentation techniques, for example the region growing technique. In one preferred refinement of at least one embodiment, the segmentation is carried out by first of all determining a profile of the central axis of the selected vessels of the vessel structure, and by calculating the axial slices along the central axis from the 3D image data record. The boundary lines of the vessel structure and of the plaque deposits are then determined from the image data for the individual axial slices.

This determination process can be carried out either by the user marking these boundary lines in the displayed axial slices or else by way of an automatic image processing algorithm, which determines the boundary lines, for example on the basis of a threshold value method, with respect to the HU value or the grey scale value of the respective pixels. A combination of an image processing algorithm with interaction by the user is also possible.

Interaction is particularly useful for determination of the boundary lines of the plaque deposits, which a viewer has until now been able to identify more reliably than is possible when using an automatic image processing algorithm. The profile of the central axis of the vessel can, of course, also be determined both interactively and by way of an appropriate image processing algorithm from the 3D image data.

The production of the synthetic 3D image model from the segmented image data is carried out by interpolation between the pixels of the vessel structure and of the plaque deposits in the segmented image data. In this case, the only pixels which are considered are those relating to the boundary lines or boundary surfaces of the vessel structure and of the plaque deposit. The interpolation process is carried out on the one hand in order to obtain a uniform grid of pixels for the production of the 3D model, and on the other hand in order to make it possible to display the model with better resolution than the 3D image data. In addition to simple linear interpolation, it is, of course, also possible to use more complex interpolation techniques in this case. The synthetic 3D image model is in this case preferably produced as a 3D polygonal network, and is then visualized in this form.

Although the present description refers primarily to the application for CT angiography, at least one embodiment of the method may, of course, also be used for 3D image data records of vessel structures which have been recorded using other imaging techniques. Examples of this are magnetic resonance tomography (MR), PET (positron emission topography), SPECT (single photon emission computed tomography) or ultrasound. The only precondition for the use of at least one embodiment of the method is that it is possible to segment the recorded vessel structure as well as the plaque deposits from the 3D image data record.

BRIEF DESCRIPTION OF THE DRAWINGS

The method will be explained once again in brief in the following text with reference to one example embodiment and in conjunction with the drawings, without any restriction to the area of protection specified by the patent claims. In this case, in a highly schematic illustrative form:

DETAILED DESCRIPTION OF THE EXAMPLE EMBODIMENTS

Figure 1:
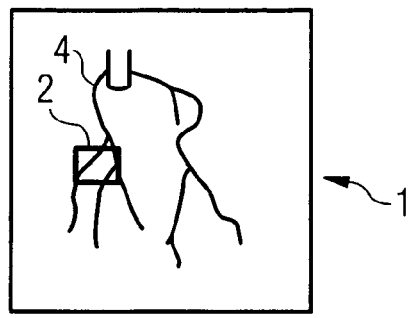
FIG. 1 shows an example of a display of the CT record of a coronary vessel structure.

The method will be explained by way of example in the following text on the basis of the visualization of a vessel section of the coronary vessel structure of a patient, as can be recorded using a modern multiple-layer CT appliance, using the CT angiography technique. In this context, FIG. 1 shows one example of an illustration in the form of a figure of the 3D image data record obtained by way of CT angiography, indicating the coronary vessel structure 4. From this image, the user chooses a detail 2 which contains a vessel section to be examined in more detail. This selection is made interactively, with the user generally having the capability to interactively select the suitable perspective and way of displaying the CT image 1, in particular by three-dimensional variation of the orientation of the image, in order possibly to identify vessel sections affected by plaque.

Figure 2:
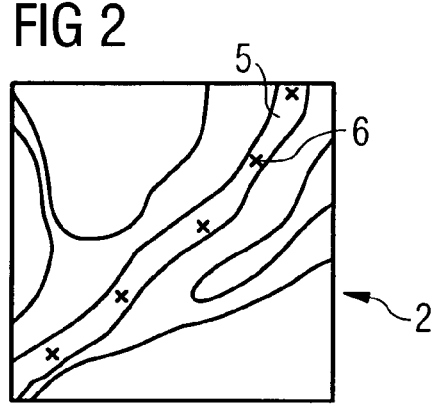
FIG. 2 shows an example of a detail enlargement from the display in FIG. 1.

After the selection of the vessel section to be analyzed, the user interactively marks the central axis of the vessel section 5 in the detail enlargement 2 which is illustrated by way of example in FIG. 2. The markings 6 which are applied for this purpose can be seen in FIG. 2.

Alternatively, the central vessel axis can also be determined automatically by known image processing algorithms. This can be done without any problems particularly in the case of CT image recording of vessels enriched with contrast agent on the basis of the increase in contrast associated with this, possibly after removal of a mask image when using subtraction angiography.

Figure 3:
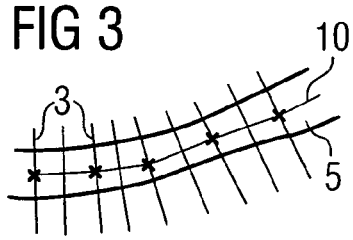
FIG. 3 shows an example of the arrangement of axial slices through the central profile of a vessel.

Axial slices 3 through this vessel section 5 are then calculated on the basis of the profile of the central axis 10 of the vessel section 5 determined in this way, as is illustrated in FIG. 3.

Figure 4:
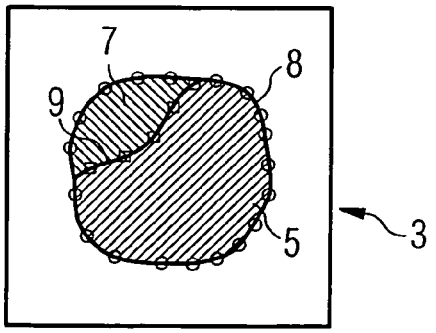
FIG. 4 shows an example of an axial slice image in each of the vessels.

In the next step, these axial slices 3 are displayed successively to the user as slice images. FIG. 4 shows one example of an axial slice image such as this. The user interactively marks the boundary lines 9 of the plaque deposits 7 in this image (indicated by the squares in FIG. 4). The boundary lines 8 of the vessel section 5 are marked in the same way, either interactively or with the aid of an automatic segmentation algorithm (circles in FIG. 4).

After carrying out this step for all the axial slices 3 of the vessel section 5, the boundary points of the vessel section 5 and of the plaque deposits 7 are evident in this vessel section. An interpolation process is carried out on the basis of these boundary points, which may occur at three-dimensional distances of different size depending on the three-dimensional resolution of the original CT record as well as the marking points that have been marked, in order to produce a synthetic three-dimensional model of the boundary surfaces of the vessel section, and of the plaque deposits, with high resolution. This synthetic three-dimensional model is represented by a polygonal network, for example a triangular network, which forms the respective boundary surfaces.

Figure 5:
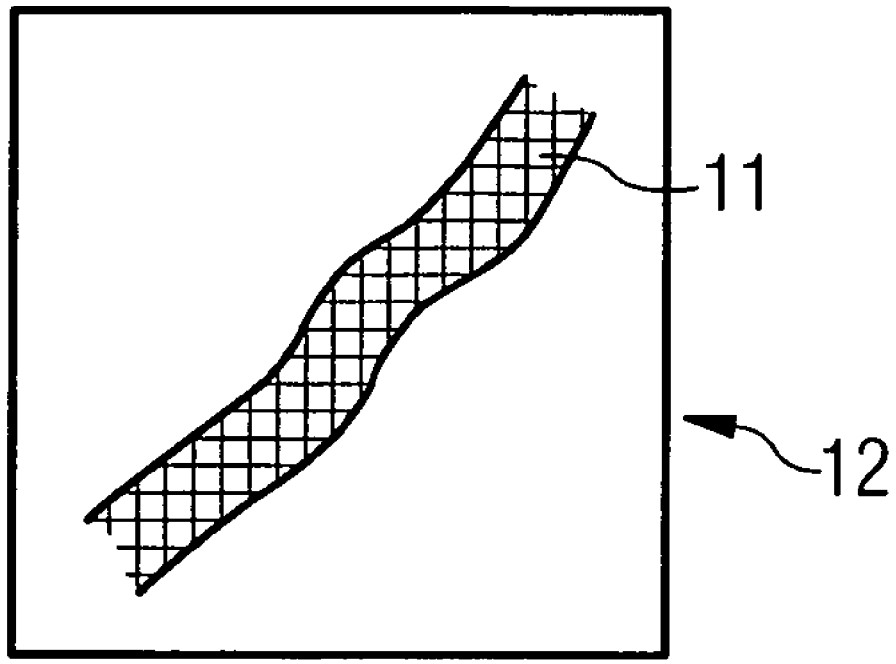
FIG. 5 shows two examples of the display of the synthetic 3D model.
Figure 5:
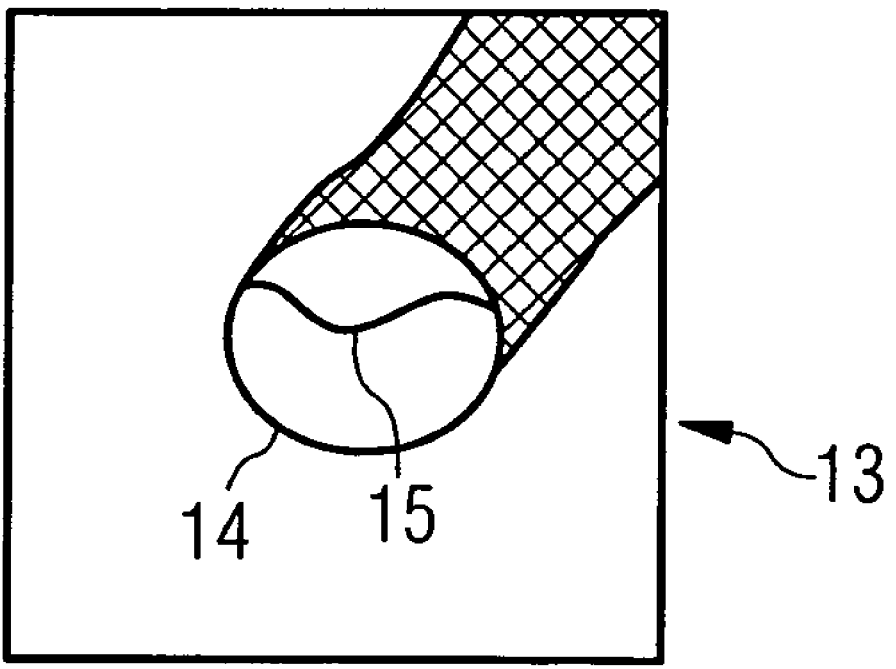

The three-dimensional model which is produced in this way is then visualized in a suitable manner and/or in a manner which can be predetermined, as is indicated in a highly schematic form in the two illustrations 12, 13 in FIG. 5. These illustrations show the polygonal network 11 as well as boundary surfaces 14 of the vessel section formed in this way, as well as the boundary surfaces 15 of the plaque deposit.

This technique allows the user to clearly visualize the visual section as well as the plaque deposit located in it, with chronic three-dimensional resolution. The user can in this case analyze the three-dimensional relationships between the plaque deposit and the vessel wall or of the vessel lumen in real time from different perspectives and, in particular, can move through the display of the 3D model even in real time. In the process, he is provided with a more realistic impression of the geometric relationships of a stenosis and of the way in which the blood flow is influenced by the stenosis.

The above described embodiments of the method may further be embodied in a physical device, as would be understood by one of ordinary skill in the art, including via use of the disclosed and/or illustrated examples.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualization of plaque deposits from 3D image data records of vessel structures in which at least one section of the vessel structure with the plaque deposits is segmented in the 3D image data record in order to obtain segmented image data, the method comprising:

producing a synthetic 3D model image of the at least one section of the vessel structure and of the plaque deposits from the segmented image data, the synthetic 3D model image including only boundary surfaces of the vessel structure and of the plaque deposits, the synthetic 3D model image being produced by three-dimensional interpolation between pixels associated with boundary surfaces of the vessel structure, and between pixels associated with boundary surfaces of the plaque deposits in order to obtain a uniform grid at pixels for the 3D model image, wherein at least a partial image of the synthetic 3D model image is visualized.

2. The method as claimed in claim 1, wherein the segmentation is carried out by:
   determining a profile of a central axis of the at least one section of the vessel structure,
   calculating axial slices along the central axis, and
   determining boundary lines of the at least one section of the vessel structure and of the plaque deposits from image data from the axial slices.

3. The method as claimed in claim 1, wherein the synthetic 3D model image is produced and visualized as a polygonal network.

4. The method as claimed in claim 1, wherein at least one of the viewing perspective and virtual movement is changeable by the at least one section of the vessel structure in real time.

5. The method as claimed in claim 1, wherein the method is for visualization of plaque deposits from 3D image data records of vessel structures of the coronary vascular system.

6. The method as claimed in claim 2, wherein the synthetic 3D model image is produced and visualized as a polygonal network.

7. The method as claimed in claim 2, wherein at least one of the viewing perspective and virtual movement is changeable by the at least one section of the vessel structure in real time.

8. The method as claimed in claim 3, wherein at least one of the viewing perspective and virtual movement is changeable by the at least one section of the vessel structure in real time.

9. The method as claimed in claim 6, wherein at least one of the viewing perspective and virtual movement is changeable by the at least one section of the vessel structure in real time.

10. A method for visualization of plaque deposits from 3D image data records of vessel structures in which at least one section of the vessel structure, comprising:
    segmenting the plaque deposits in the 3D image data record to obtain segmented image data; and
    producing a synthetic 3D model image of the at least one section of the vessel structure and of the plaque deposits from the segmented image data, the synthetic 3D model image including only boundary surfaces of the vessel structure and of the plaque deposits, the synthetic 3D model image being produced by three-dimensional interpolation between pixels associated with boundary surfaces of the vessel structure and between pixels associated with boundary surfaces of the plaque deposits, to obtain a uniform grid at pixels for the 3D model image.

11. The method as claimed in claim 10, wherein the segmentation is carried out by:
    determining a profile of a central axis of the at least one section of the vessel structure,
    calculating axial slices along the central axis, and
    determining boundary lines of the at least one section of the vessel structure and of the plaque deposits from image data from the axial slices.

12. The method as claimed in claim 10, wherein the synthetic 3D model image is produced and visualized as a polygonal network.

13. The method as claimed in claim 10, wherein at least one of the viewing perspective and virtual movement is changeable by the at least one section of the vessel structure in real time.

14. The method as claimed in claim 10, wherein the method is for visualization of plaque deposits from 3D image data records of vessel structures of the coronary vascular system.

15. The method as claimed in claim 11, wherein the synthetic 3D model image is produced and visualized as a polygonal network.

16. The method as claimed in claim 11, wherein at least one of the viewing perspective and virtual movement is changeable by the at least one section of the vessel structure in real time.

17. The method as claimed in claim 12, wherein at least one of the viewing perspective and virtual movement is changeable by the at least one section of the vessel structure in real time.

18. The method as claimed in claim 15, wherein at least one of the viewing perspective and virtual movement is changeable by the at least one section of the vessel structure in real time.

19. The method as claimed in claim 10, wherein at least a partial image of the synthetic 3D model image is visualized.

20. The method as claimed in claim 10, further comprising: visualizing at least a partial image of the synthetic 3D model image.

* * * * *